United States Patent [19]

Moloy et al.

[11] Patent Number: 5,264,606
[45] Date of Patent: Nov. 23, 1993

[54] PROCESS FOR THE PREPARATION OF POLYVINYL COMPOUNDS

[75] Inventors: Kenneth G. Moloy; Bernard D. Dombek, both of Charleston, W. Va.

[73] Assignee: Union Carbide Chemicals & Plastics Technology Corporation, Danbury, Conn.

[21] Appl. No.: 973,984

[22] Filed: Nov. 9, 1992

Related U.S. Application Data

[63] Continuation of Ser. No. 594,001, Oct. 9, 1990.

[51] Int. Cl.$^5$ .......................... C07C 4/06; C07C 4/08; C07C 6/06; C07F 7/02
[52] U.S. Cl. ...................... 556/482; 585/353; 585/374; 560/125; 558/432; 564/189; 564/191; 564/453; 568/816
[58] Field of Search ............... 585/374, 353; 556/482; 560/121, 125, 126, 128, 129; 558/432; 564/189, 191, 441, 444, 453; 568/443, 445, 664, 666, 816, 838

[56] References Cited

U.S. PATENT DOCUMENTS

| | | | |
|---|---|---|---|
| 2,975,202 | 3/1961 | Miyer | 556/460 |
| 3,424,811 | 1/1969 | Mango | 260/680 |
| 3,925,249 | 12/1975 | Fitton et al. | 252/430 |
| 4,497,943 | 2/1985 | Takago et al. | 556/460 |
| 4,894,181 | 1/1990 | Praefcke et al. | 560/128 X |
| 5,113,003 | 5/1992 | Woods et al. | 556/482 X |
| 5,130,462 | 7/1992 | Slusarchyk et al. | 556/482 X |

FOREIGN PATENT DOCUMENTS 182333 5/1986 European Pat. Off. .

OTHER PUBLICATIONS

Dragutan et al, Olefin Metathesis etc., John Wiley & Sons, New York, 1985, 140 to 153.
Tubul et al., *Tetrahedron*, vol. 44, No. 13, pp. 3975–3982 (1988).
Jennings et al., *Journal of Organometallic Chemistry*, vol. 285, Nos. 1–3, pp. 429–436, Apr. 1985.
Finkelshtein et al., *Makromol. Chem.*, 192, 1–9 (1991).

*Primary Examiner*—Arthur C. Prescott
*Attorney, Agent, or Firm*—S. H. Hegedus

[57] ABSTRACT

A process for the preparation of monomeric polyvinyl compounds and/or oligomers thereof comprising:
  (i) preactivating a supported rhenium oxide catalyst with a hydrocarbyl metal compound; and
  (ii) reacting, under metathesis reaction conditions, norbornene or one or more substituted norbornenes, or mixtures thereof, with ethylene in the presence of the activated supported catalyst of step (i).

30 Claims, No Drawings

PROCESS FOR THE PREPARATION OF POLYVINYL COMPOUNDS

This application is a continuation of prior U.S. application: Ser. No. 07/594,001 filing date Oct. 9, 1990.

TECHNICAL FIELD

This invention relates to a process for the preparation of monomeric polyvinyl compounds and their oligomers.

BACKGROUND INFORMATION

The metathesis (or disproportionation) of cyclic olefins is a well known technique for preparing divinyl or other polyvinyl compounds. See Dragutan et al, Olefin Metathesis and Ring-Opening Polymerization of Cyclo-Olefins, John Wiley and Sons Limited, New York, 1985, pages 140 to 153, particularly pages 141 and 143. On page 141, the reaction of norbornene and ethylene in the presence of a cobalt molybdate catalyst to provide 1,3-divinyl-cyclopentane is mentioned and, on page 143, a metathesis catalyst, $WOCl_4 \cdot Sn(C_4H_9)_4$, is disclosed.

Polyvinyl compounds, particularly divinyl compounds (alpha, omega-dienes), are important precursors for a variety of compounds having two or more functionalities. These compounds find application as crosslinking agents and comonomers in resin and coating compositions.

While, as noted above, a large body of chemistry has been developed regarding the ring opening metathesis polymerization of norbornenes, the norbornenes have been essentially ignored as precursors for divinyl compounds on a commercial basis. This is somewhat surprising in that norbornenes have high ring strains making ring opening very favorable, and can only be explained on the basis of the present metathesis processes, which are prone to low conversions and selectivities.

DISCLOSURE OF THE INVENTION

An object of this invention, therefore, is to provide a process for the metathesis of norbornenes, which can be characterized by high conversion and selectivity.

Other objects and advantages will become apparent hereinafter.

According to the present invention, the above object is met by a process for the preparation of monomeric polyvinyl compounds and/or oligomers thereof comprising:

(i) preactivating a supported rhenium oxide catalyst with a hydrocarbyl metal compound; and (ii) reacting, under metathesis reaction conditions, norbornene or one or more substituted norbornenes, or mixtures thereof, with ethylene in the presence of the activated supported catalyst of step (i).

DESCRIPTION OF THE PREFERRED EMBODIMENT(S)

Norbornene, also known as bicyclo[2.2.1]-hept-2-ene, provides the basic structure for the cyclic olefins, which are metathesized with ethylene to provide various useful polyvinyl compounds or their oligomers. The basic norbornene structure can be substituted with one or more of the following groups: alkyl, cycloalkyl, alkenyl, cycloalkenyl, aryl, aralkyl, alkaryl, —CN, —NH$_2$, —OR', —COR', —COOR', —OH, —Si(OR')$_{3-a}$(R')$_{a'}$, —NO$_2$, —NO, and halogen wherein R' can be alkyl, cycloalkyl, aryl, alkaryl, or aralkyl and a can be 0, 1, or 2. The halogen is preferably fluorine, chlorine, bromine, or iodine, or mixtures thereof. Each substituent and R' can be the same or different. The hydrocarbon portion of the substituent group can have 1 to 30 carbon atoms and preferably has 1 to 15 carbon atoms.

The substituted norbornene can be represented by generic formula (A) set forth in Table II wherein R can be hydrogen or any of the above-mentioned groups and each R can be the same or different. Examples of substituted norbornene compounds are dicyclopentadiene; 5-vinyl-2-norbornene; 2-vinyl-5-norbornene; norbornadiene; 5-norbornene-2-carbonitrile; 5-ethylidene-2-norbornene; 5-triethoxysilyl-2-norbornene; and 5-norborn-2-yl acetate.

The molar ratio of the norbornenes to ethylene is in the range of about 0.1 to about 10 mols of norbornene compound(s) per mol of ethylene and preferably about 0.1 to about 1 mol of norbornene compound(s) per mol of ethylene. In this specification, the term "norbornene compound(s)" is considered to include all of the norbornene compounds used in the particular embodiment.

The rhenium oxide catalyst is generally rhenium heptoxide, $Re_2O_7$, because rhenium (VII) is the most stable of the rhenium oxidation states under the conditions under which these catalysts are prepared. Rhenium trioxychloride can also be used and is considered, for the purposes of this specification, to be a rhenium oxide. The rhenium oxide can be supported on any one of a number of metal oxides conventionally used as catalyst supports such as alumina, silica, magnesia, titania, zirconia, thoria, and tin oxide. Alumina ($Al_2O_3$) is a preferred support. The rhenium oxide can be present in the rhenium oxide/support combination in an amount of about 0.5 to about 15 percent by weight rhenium oxide based on the weight of the supported catalyst, i.e., support plus rhenium oxide, and is preferably in an amount of about 3 to about 12 percent by weight rhenium oxide.

The molar ratio of hydrocarbyl metal compound to rhenium in the rhenium oxide catalyst can be about 0.1 to about 10 mols of hydrocarbyl metal compound to one mole of rhenium, and is preferably about 0.5 to about 5 mols to one mole of rhenium.

The hydrocarbyl metal compounds are preferably those based on tin, aluminum, or zinc. They can have the following formulas: $R_4Sn$, $R_3Al$, $R_2AlCl$, $RAlCl_2$, and $R_2Zn$ wherein R is alkyl, aryl, alkaryl, or aralkyl and each R can be the same or different. Examples of R are methyl, ethyl, butyl, phenyl, benzyl, and tolyl. Hydrocarbyl tin compounds are most preferred. Examples of suitable hydrocarbyl metal compounds are tetramethyltin, tetraethyltin, tetrabutyltin, tetraphenyltin, tetrabenzyltin, tetratolyltin, triethylaluminum, diethylaluminum chloride, ethylaluminum dichloride, and diethylzinc. The number of carbons in each R group can be 1 to 20 and is preferably 1 to 10.

The amount of activated supported catalyst is, as a practical matter, determined by the operator of the process using as little catalyst as possible to achieve the desired result. Generally, the amount can be in the range of about 0.001 to about 5 parts by weight of activated supported catalyst (including rhenium oxide, support, and hydrocarbyl tin compound) per 100 parts by weight of norbornene compound(s), i.e., the total weight of all of the norbornene compounds introduced into a particular process run, and is preferably in the range of about 0.01 to about 1 part by weight of activated supported catalyst per 100 parts by weight of norbornene compound(s).

If desired, the catalyst can be modified or promoted with an alkali metal oxide such as potassium oxide as discussed in U.S. Pat. No. 3,424,811. This is generally accomplished by impregnating the support with, e.g., potassium carbonate, and then heating prior to the impregnation of the support with a rhenium compound. A typical procedure is provided in Example 4, below.

The process is preferably carried out in the liquid phase in a solvent which is inert to the reactants and the conditions of the process. The solvent can be an aliphatic, cycloaliphatic or aromatic hydrocarbon such as hexane, pentane, cyclohexane, isooctane, butane, benzene, napthalene, and toluene. The hydrocarbon referred to can also be halogenated, examples of halogenated hydrocarbons being chlorobenzene, methylene chloride, chloroform, and dichloroethane. Carbon tetrachloride is also useful.

The partial pressure of the ethylene in the vapor phase residing above the liquid phase in which the reaction is carried out can be in the range of about 5 psia to about 4000 psia and is preferably in the range of about 15 to about 250 psia. This pressure can also be considered the metathesis reaction pressure.

The temperature of the preactivation step can be in the range of about 0° to about 125° C. and is preferably in the range of about 15° to about 100° C. The temperature at which the norbornene/ethylene reaction, i.e., the metathesis, is conducted can be in the range of about 0° C. to about 125° C. and is preferably in the range of about 15° C. to about 100° C.

A gas phase metathesis process is not preferred because it requires volatile reactants and products. For less volatile olefins, such as the norbornenes, higher temperatures are required. Norbornenes, however, undergo cracking reactions at high temperatures yielding a cyclopentadiene and an olefin. The conjugated dienes produced in these cracking reactions can be poisons for metathesis catalysts.

A typical liquid phase metathesis reaction can be carried out using a catalyst comprised of rhenium heptoxide ($Re_2O_7$) impregnated on an alumina support. The supported catalyst is slurried in hexane and then preactivated with tetramethyltin. Norbornene and ethylene are introduced into the slurry at room temperature under an ethylene partial pressure of 250 psia. The reaction produces a mixture of oligomers, which result from secondary metathesis reactions. The higher oligomers result from the metathesis reaction of the initially formed cis-1,3-divinylcyclopentane with additional equivalents of norbornene. All of the oligomers are in dynamic equilibrium with each other. Thus, the equilibrium can be shifted to whatever oligomer is desired. This can be accomplished by varying the ratio of norbornene and ethylene or selectively removing the desired product from the reaction zone and recycling the other components. The equations illustrating this oligomerization are set forth under (C) in Table III. Because of the dynamic equilibria, the formation of oligomers does not represent a loss of starting material; the oligomers can simply be recycled and eventually converted to a single product.

The metathesis reactions of norbornene compounds with ethylene to produce divinyl and trivinyl compounds are also shown in Table III. See equations (D) to (I).

Novel compounds prepared by the process of the invention can have generic formula (B) set forth in Table II. It will be noted that the generic formula is a cis compound as signified by the wedge-shaped lines. There are also at least two vinyl groups present. R can be hydrogen provided that at least one R is an alkyl, cycloalkyl, alkenyl, cycloalkyl, aryl, aralkyl, alkaryl —CN, —$NH_2$, —OR', —COR', —COOR', —OH, —Si(OR')$_{3-a}$(R')$_a$, —$NO_2$, —NO, or halogen wherein R' can be alkyl, cycloalkyl, aryl, alkaryl, or aralkyl and a can be 0, 1, or 2. Each R and R' can be the same or different. The halogen is preferably fluorine, chlorine, bromine, or iodine, or mixtures thereof.

Polyvinyl compounds produced by the process of the invention are cis-1,3-divinylcyclopentane;
1,2,4-trivinylcyclopentane; 3,5-divinylcyclopentene;
2,4-divinylcyclo[3.3.0]oct-6-ene;
1,3-divinyl-4-ethylidenecyclopentane;
2,4-divinylcyclopentane carbonitrile;
1,3-divinyl-4-triethoxysilylcyclopentane;
2,4-divinylcyclopentyl acetate;
phenyl-2,4-divinylcyclopentane;
benzyl-2,4-divinylcyclopentane;
N,N-dimethylamino-2,4-divinylcyclopentane;
ethoxy-2,4-divinylcyclopentane;
2,4-divinylcyclopentanecarboxaldehyde;
2,4-divinylcyclopentyl methyl ketone;
methyl-2,4-divinylcyclopentanecarboxylate;
hydroxy-2,4-divinylcyclopentane;
nitro-2,4-divinylcyclopentane;
nitroso-2,4-divinylcyclopentane; and
chloro-2,4-divinylcyclopentane.

The norbornenes are readily prepared by the Diels-Alder reaction of, e.g., cyclopentadiene (obtained by cracking the dimer) with the appropriate olefin. Thus, norbornene can be prepared from dicyclopentadiene (cracked in situ to monomer) and ethylene in yields of up to 71 percent by weight. Diels-Alder reactions are discussed in Streitweiser et al, Introduction to Organic Chemistry, 3rd edition, Macmillan Publishing Company, New York, 1985, pages 550 to 556.

The publications and patent mentioned in this specification are incorporated by reference herein.

The invention is illustrated by the following examples.

EXAMPLE 1

In a typical procedure an $Re_2O_7/Al_2O_3$ supported catalyst is prepared by contacting a solution of 8.2 grams of rhenium (VII) oxide in 55.9 milliliters of water with 120 grams of gamma-alumina having a surface area of 210 square meters per gram and a pore volume of 0.47 milliliter per gram. The catalyst is allowed to stand for 0.5 hour, mixed well, allowed to stand for another 0.5 hour, and dried at 120° C. It is then activated by heating to 550° C. under a steady flow of oxygen for 3 hours followed by a steady flow of nitrogen at the same temperature for an additional 3 hours. The $Re_2O_7$ is 6 percent by weight based on the total composition, i.e., $Re_2O_7/Al_2O_3$. The supported catalyst is then cooled to room temperature and stored under anhydrous conditions.

EXAMPLE 2

This example shows the low conversion obtained using a conventional preactivation technique.

1 gram of the activated supported catalyst prepared in Example 1 and 5 milliliters of hexane are charged to a pressure reactor, which is then sealed and pressurized with 4,750 psi of ethylene. Next, a mixture of 5 milliliters of norbornene in 19 milliliters of hexane is pumped into the reactor over a 20 minute period with stirring. The reactor and its contents are maintained at ambient temperature throughout the experiment. After stirring for another 2.5 hours, gas chromatograph analysis shows a 1.9 percent by weight conversion to 1,3-divinylcyclopentane and higher oligomers.

The product is analyzed on a Hewlett Packard 5890 chromatograph with a flame ionization detector and a 30 meter Durabond 1701 capillary column programmed at 150° C. for 2 minutes and then ramped to 275° C. at 20° C./minute. This procedure is followed for gas chromatograph analysis throughout.

EXAMPLE 3

This example also shows the low conversion (in this case, no conversion) obtained using a conventional preactivation technique.

Example 2 is repeated except as follows: A solution of 5 milliliters of 5-vinyl-2-norbornene in 20 milliliters of hexane is added to 1 gram of activated supported catalyst in 5 milliliters of hexane. The reactor is pressurized to 4300 psi with ethylene. After stirring overnight at 21° C., gas chromatograph analysis shows no conversion to product.

EXAMPLE 4

This example shows the low conversion obtained using a conventional preactivation together with catalyst modification with an alkali metal oxide.

10 grams of the same gamma alumina as that used in Example 1 are impregnated with a solution of 0.06 gram $K_2CO_3$ in 4.7 milliliters of water. The resulting material is then dried at 130° C. and impregnated with a solution of 0.78 gram $NH_4ReO_4$ in 4.7 milliliters of warm water. The solid is heated to 130° C. followed by heating at 550° C. for 3 hours under a steady flow of oxygen and then for 3 hours under a steady flow of nitrogen. The resulting activated supported catalyst is cooled to room temperature and stored under anhydrous conditions.

One gram of this $K_2O/Re_2O_7/Al_2O_3$ catalyst and 5 milliliters of hexane are charged to the reactor. The reactor is pressurized with 500 psi ethylene and then 27 milliliters of a solution of 5 grams of norbornene in 20 milliliters of hexane are pumped in, with stirring, over the course of 2 hours. Stirring is continued for an additional 2 hours and then the product is analyzed. Gas chromatograph analysis shows a 1 percent by weight conversion to product.

EXAMPLE 5

Example 2 is repeated except as follows. In this example, the activated supported catalyst prepared as in Example 1 is further activated with a hydrocarbyl tin compound in the pressure reactor prior to pressurizing with ethylene. The catalyst is activated by adding 0.034 milliliter of tetramethyltin, under nitrogen, with stirring. The reaction is then pressurized with 3,300 psi of ethylene after which a solution of 5 milliliters of norbornene in 20.4 milliliters of hexane is pumped in, at ambient temperature (internal reactor temperature), over a 2 hour period with stirring. After an additional 2 hours of stirring, the resulting liquid is sampled and analyzed by gas chromatography.

The analysis shows 99.7 percent by weight conversion of the norbornene to cis-1,3-divinylcyclopentane and higher oligomers. The selectivity to metathesis product is 100 percent.

EXAMPLE 6

Example 5 is repeated except as follows: 5-vinyl-2-norbornene is reacted with ethylene at 3800 psi and 25° C. The conversion is 85 percent by weight and the selectivity to trivinylcyclopentane and higher oligomers is 100 percent.

EXAMPLE 7

Example 5 is repeated except as follows: A 5 gallon stirred autoclave, which has been purged with nitrogen, is used. 213 grams of supported catalyst, 8 liters of hexane, and 7.5 milliliters of tetramethyltin are used. After catalyst activation, the reactor is sealed, pressure tested with nitrogen, and pressurized to 800 psi with ethylene. A solution of 1500 grams norbornene in 1.8 liters of hexane is then pumped into the reactor over an 8 hour period. The reactor is vented when necessary to keep the pressure below 1400 psi. The reactor is stirred for an additional 13 hours and the autoclave is then vented. Gas chromatograph analysis shows 99.8 percent by weight conversion to metathesis product. Pure cis-1,3-divinylcyclopentane is isolated by distillation at 140° to 142° C., 760 torr, in accordance with the literature. The nuclear magnetic resonance and infrared spectra of this product are also in agreement with the literature.

EXAMPLE 8

A 5 gallon autoclave is heated to 100° C. under a steady purge of nitrogen. After cooling to ambient temperature, the autoclave is charged with 692 grams of supported catalyst (10 percent by weight $Re_2O_7$/balance $Al_2O_3$; 1/16 inch spheres; prepared as in Example 1) and 3 liters of dry hexane. 37 milliliters of tetramethyltin is added and the mixture is stirred under nitrogen for 10 minutes. Then, a solution of 4500 grams of norbornene in 2.8 liters of hexane is poured into the autoclave. The autoclave is sealed, pressurized to 3000 psia with ethylene, and the reactor is stirred at ambient temperature. The pressure is gradually dropped and held at a final pressure of 700 to 800 psia by adding additional ethylene as needed. After 26 hours, the autoclave contents are analyzed by gas chromatography. The analysis shows a norbornene conversion of greater than 99 percent by weight with a selectivity to metathesis product of 100 percent. The cis-1,3-divinylcyclopentane is isolated and purified by distillation as in Example 7.

EXAMPLE 9

Example 8 is repeated except as follows: 2000 grams of 5-vinyl-2-norbornene is metathesized to trivinylcyclopentane using 540 grams of $Re_2O_7/Al_2O_3$ catalyst, 18 milliliters of tetramethyltin, and 10 liters of hexane. The metathesis temperature is 20° to 25° C. and the metathesis pressure is maintained at 650 to 1400 psia. After stirring overnight, the gas chromatograph analysis shows the vinyl norbornene conversion to be 95 percent by weight and the selectivity to metathesis product to be 100 percent. The resulting 1,2,4-trivinylcyclopentane is purified by distillation at 47° C., 8 millimeters of mercury, with a 10 tray Oldershaw column.

EXAMPLE 10

Example 5 is repeated except as follows: 1 gram of potassium promoted $Re_2O_7/Al_2O_3$ catalyst in 10 milliliters of hexane is activated with 0.034 milliliter of tetramethyltin. The reactor is pressurized with 800 psi ethylene, and then a solution of 7 milliliters of norbornene in 7 milliliters of hexane is added over a 1 hour period. After stirring for an additional 2 hours, gas chromatograph analysis shows a conversion of 54 percent by weight. The selectivity to cis-1,3-divinylcyclopentane and oligomers is 100 percent.

EXAMPLE 11

Example 5 is repeated except as follows: Norbornadiene is metathesized to cis-3,5-divinylcyclopentene. After 3 hours at 25° C. and 750 psia, gas chromatograph analysis shows a 65 percent by weight conversion to metathesis products with 100 percent selectivity.

EXAMPLE 12

Example 5 is repeated except as follows: 4,5-norbornene-2-carbonitrile is metathesized to cis-2,5-divinylcyclopentanecarbonitrile. The selectivity is 100 percent.

EXAMPLE 13

Example 5 is repeated except as follows: 5-ethylidene-2-norbornene is metathesized to cis-1,3-divinyl-4-ethylidenecyclopentane. The conversion, after reacting overnight, is 31 percent by weight and the selectivity is 100 percent.

EXAMPLE 14

Example 5 is repeated except as follows: Dicyclopentadiene is metathesized to cis-2,4-divinylbicyclo[3.3.0]oct-7-ene using 2 grams of catalyst; 0.08 milliliter tetramethyltin; and 5 milliliters of dicyclopentadiene. The selectivity is 100 percent and the conversion after 16 hours of reaction at room temperature is 60 percent.

EXAMPLE 15

Example 5 is repeated except as follows: A reactor is charged with 2 grams of $Re_2O_7/Al_2O_3$ catalyst, 5 milliliters of hexane, and 0.08 milliliters of tetramethyltin. The reactor is sealed and pressurized to 635 psia with ethylene, and then heated to a temperature of 60° C. A solution of 5 milliliters of dicyclopentadiene in 20 milliliters of hexane is then fed to the reactor over a 2.5 hour period. Aliquots are periodically removed for analysis. After 23 hours, the conversion is 60 percent by weight, and the selectivity to cis-2,4-divinylbicyclo[3.3.0]oct-7-ene is 100 percent.

EXAMPLE 16

Example 5 is repeated except as follows: A reactor is charged with 1 gram $Re_2O_7/Al_2O_3$ catalyst, 5 milliliters of toluene, and 0.04 milliliter of tetramethyltin. After sealing and pressurizing with 555 psi ethylene, a solution of 2.5 milliliters of dicyclopentadiene in 20 milliliters of toluene is pumped into the reactor over a period of 2 hours. After stirring overnight at room temperature, the conversion is 25 percent by weight and the selectivity is 100 percent.

EXAMPLE 17

Example 5 is repeated except as follows: Norbornene is metathesized at a variety of ethylene pressures. The product distributions obtained are set forth in Table I.

TABLE I

| ethylene pressure (psia) | divinylcyclopentane | dimer | trimer |
|---|---|---|---|
| | (percent by weight) | | |
| 4000 | 76.3 | 17.3 | 6.5 |
| 2000 | 70.7 | 21.5 | 7.8 |

TABLE I-continued

| ethylene pressure (psia) | divinylcyclopentane | dimer | trimer |
|---|---|---|---|
| | (percent by weight) | | |
| 1000 | 79.2 | 14.8 | 6.1 |
| 500 | 69.6 | 22.6 | 7.8 |
| 280 | 79.0 | 16.4 | 4.7 |
| 150 | 68.4 | 23.8 | 7.8 |
| 50 | 67.0 | 27.0 | 6.5 |

This example shows that ethylene pressure has little effect on product distribution. Higher norbornene concentrations and lower ethylene pressures lead to greater amounts of dimer, trimer, and heavier oligomers.

EXAMPLE 18

Example 5 is repeated except as follows: 5-triethoxysilyl-2-norbornene is metathesized to cis-1,3-divinyl-4-triethoxysilylcyclopentane. The conversion, after reacting overnight, is 11 percent by weight and the selectivity is 100 percent.

EXAMPLE 19

Example 5 is repeated except as follows: 5-norbornene-2-yl acetate is metathesized to cis-2,4-divinylcyclopentyl acetate. The conversion, after reacting overnight, is 21 percent by weight and the selectivity is 100 percent.

TABLE II

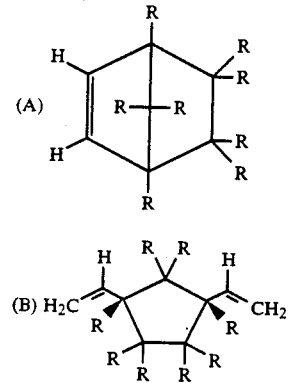

TABLE III

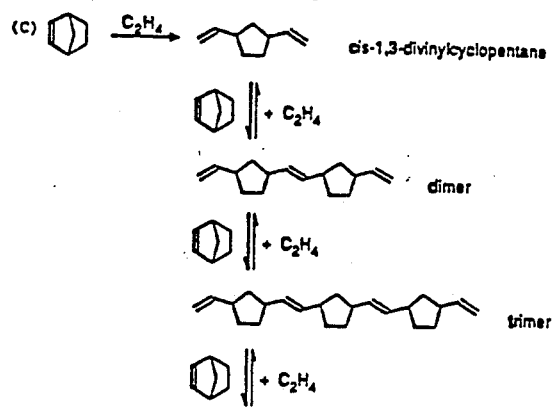

TABLE III (continued)

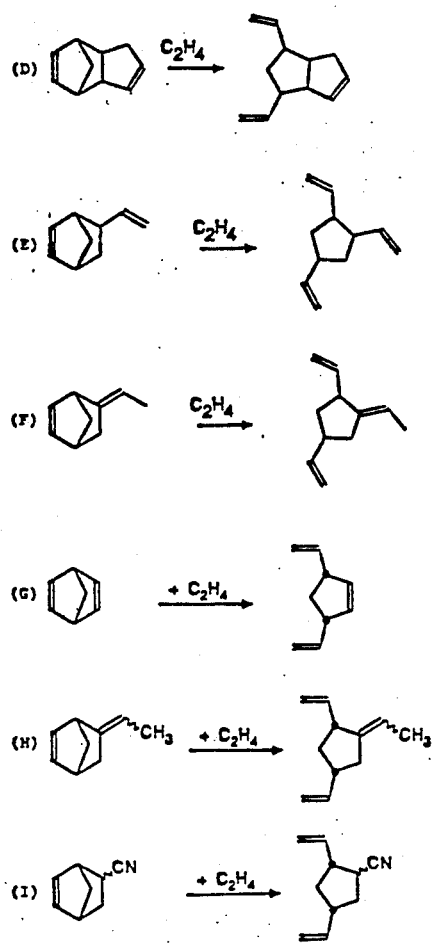

We claim:
1. A process for the production of polyvinyl compounds, oligomers thereof and mixtures thereof which comprises reacting norbornene, substituted norbornene or a mixture thereof with ethylene in the presence of a hydrocarbyl metal activated supported rhenium oxide catalyst.

2. A process for the production of polyvinyl compounds of the formula:

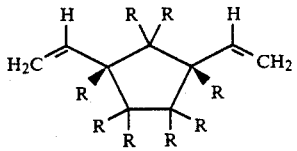

and oligomers and mixtures thereof which comprises reacting in the presence of a hydrocarbyl metal activated supported rhenium oxide catalyst, ethylene and a norbornene compound of the formula:

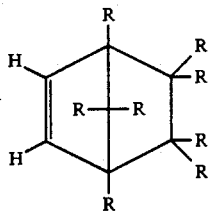

wherein:
R is independently hydrogen, alkyl, cycloalkyl, alkenyl, cycloalkenyl, aryl, aralkyl, alkaryl, —CN, —NH$_2$, —OR', —COR', COOR', —OH, —Si(OR')$_{3-a}$(R')$_a$, —NO$_2$, —NO, or halogen;
R' is independently alkyl, cycloalkyl, aryl, alkaryl, or aralkyl; and
a is 0, 1 or 2;
with the proviso that at least one R is other than hydrogen.

3. A process for the preparation of monomeric polyvinyl compounds and/or oligomers thereof comprising:
(i) preactivating a supported rhenium oxide catalyst with a hydrocarbyl metal compound; and
(ii) reacting, under metathesis reaction conditions, norbornene or one or more substituted norbornenes, or mixtures thereof, with ethylene in the presence of the activated supported catalyst of step (i).

4. The process defined in claim 1 wherein the support is a metal oxide.

5. The process defined in claim 4 wherein the metal oxide is alumina, silica, or magnesia.

6. The process defined in claim 1 wherein the rhenium oxide is rhenium heptoxide.

7. The process defined in claim 3 wherein the hydrocarbyl metal compound has the formula R$_4$Sn, R$_3$Al, R$_2$AlCl, RAlCl$_2$, or R$_2$Zn wherein R is alkyl, aryl, alkaryl, or aralkyl and each R can be the same or different.

8. The process defined in claim 7 wherein R is alkyl and has 1 to 20 carbon atoms.

9. The process defined in claim 1 effected in the liquid phase.

10. The process defined in claim 3 effected in a hydrocarbon or halogenated hydrocarbon solvent inert to the activation or metathesis reactions.

11. The process defined in claim 3 wherein step (ii) is carried out at a temperature in the range of about 0° C. to about 125° C.

12. The process defined in claim 11 wherein the temperature is in the range of about 15° C. to about 100° C.

13. The process defined in claim 3 wherein the metathesis reaction pressure is in the range of about 5 psia to about 4000 psia.

14. The process defined in claim 13 wherein the pressure is in the range of about 15 psia to about 250 psia.

15. The process defined in claim 3 wherein norbornene is reacted in step (ii).

16. The process defined in claim 1 wherein the norbornene compound reacted is a substituted norbornene.

17. The process defined in claim 16 wherein the substituted norbornene has one or more substituents, which can be the same or different.

18. The process defined in claim 17 wherein at least one of the substituents is a hydrocarbyl group having 1 to 30 carbon atoms.

19. The process defined in claim 17 wherein the substituents are alkyl, cycloalkyl, alkenyl, cycloalkenyl, aryl, alkaryl, aralkyl, —CN, —NH$_2$, —OR', —COR', COOR', —OH, —Si(OR')$_{3-a}$(R')$_a$, —NO$_2$, —NO, or halogen and R' is alkyl, cycloalkyl, aryl, alkaryl, or aralkyl; a is 0, 1 or 2, and each substituent and R' are the same or different.

20. The process defined in claim 1 wherein the molar ratio of norbornene compound(s) to ethylene is in the range of about 0.1 to about 10 mols of norbornene compound(s) per mol of ethylene.

21. The process defined in claim 1 wherein the rhenium oxide is present in the supported catalyst in an amount of about 0.5 to about 15 percent by weight based on the weight of the supported catalyst.

22. The process defined in claim 1 wherein there are about 0.1 to about 10 mols of hydrocarbyl metal compound per mol of rhenium.

23. The product of the process defined in claim 1.

24. 1,2,4-trivinylcyclopentane.

25. 2,4-divinylcyclo[3.3.0]oct-6-ene.

26. 1,3-divinyl-4-ethylidenecyclopentane.

27. 2,4-divinylcyclopentane carbonitrile.

28. 1,3-divinyl-4-triethoxysilylcyclopentane.

29. 2,4-divinylcyclopentyl acetate.

30. A process for the production of 1,2,4-trivinylcyclopentane which comprises reacting 5-vinyl-2-norbornene with ethylene in the presence of $Re_2O_7/Al_2O_3$ catalyst and tetramethyltin at a temperature of 20° C. to 25° C. and a pressure of 650 psia to 1400 psia.

* * * * *